(12) United States Patent
Govari et al.

(10) Patent No.: US 12,245,802 B2
(45) Date of Patent: *Mar. 11, 2025

(54) GENERATING IRREVERSIBLE ELECTROPORATION AND RADIOFREQUENCY-ABALTION (IRE/RFA) WAVEFORMS

(71) Applicant: Biosense Webster (Israel) Ltd., Yokneam (IL)

(72) Inventors: Assaf Govari, Haifa (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 121 days.

This patent is subject to a terminal disclaimer.

(21) Appl. No.: 18/302,109

(22) Filed: Apr. 18, 2023

(65) Prior Publication Data

US 2023/0248412 A1    Aug. 10, 2023

Related U.S. Application Data

(63) Continuation of application No. 16/704,421, filed on Dec. 5, 2019, now Pat. No. 11,660,135.

(51) Int. Cl.
*A61B 18/12* (2006.01)
*A61B 18/00* (2006.01)
*A61N 1/32* (2006.01)

(52) U.S. Cl.
CPC .......... *A61B 18/1233* (2013.01); *A61N 1/327* (2013.01); *A61B 2018/00577* (2013.01);
(Continued)

(58) Field of Classification Search
None
See application file for complete search history.

(56) References Cited

U.S. PATENT DOCUMENTS 8,048,067 B2    11/2011    Davalos et al.
8,221,411 B2    7/2012    Franischelli et al.
(Continued)

FOREIGN PATENT DOCUMENTS

EP    2469699 A2    6/2012
EP    3248561 A1    11/2017
(Continued)

OTHER PUBLICATIONS

International Search Report and Written Opinion from corresponding International Patent Application No. PCT/IB2020/050677, dated Aug. 13, 2020.
(Continued)

*Primary Examiner* — Sean W Collins
*Assistant Examiner* — Nora W Rhodes
(74) *Attorney, Agent, or Firm* — Dergosits & Noah LLP; Todd A. Noah

(57) ABSTRACT

An irreversible electroporation and radio frequency ablation (IRE/RFA) generator includes an IRE pulse generator, harmonic filtration circuitry, and a waveform interleaver. The IRE pulse generator is configured to generate biphasic IRE pulses. The harmonic filtration circuitry is configured to convert the IRE pulses into an RF signal. The waveform interleaver, which is configured to receive the IRE pulses and the RF signal and generate an output signal having a composition of the adapted IRE pulses having a final shape and repetition rate, the converted RF sinusoidal signal, or a combined IRE/RFA output signal, by switching between the received IRE square pulses and the received converted RF sinusoidal signal.

15 Claims, 3 Drawing Sheets

(52) U.S. Cl.
CPC . *A61B 2018/00613* (2013.01); *A61B 18/1206* (2013.01); *A61B 2018/1266* (2013.01)

(56) References Cited

U.S. PATENT DOCUMENTS

| | | | |
|---|---|---|---|
| 9,289,606 | B2 | 3/2016 | Paul et al. |
| 9,333,034 | B2 | 5/2016 | Hancock |
| 9,474,574 | B2 | 10/2016 | Ibrahim et al. |
| 9,717,552 | B2 | 8/2017 | Cosman et al. |
| 10,258,406 | B2 | 4/2019 | Long |
| 10,271,893 | B2 | 4/2019 | Stewart et al. |
| 10,342,598 | B2 | 7/2019 | Long et al. |
| 10,531,914 | B2 | 1/2020 | Stewart et al. |
| 11,033,236 | B2 | 6/2021 | Viswanathan et al. |
| 11,284,933 | B2 | 3/2022 | Hancock et al. |
| 2004/0260279 | A1 | 12/2004 | Goble et al. |
| 2014/0066913 | A1 | 3/2014 | Sherman |
| 2016/0051324 | A1 | 2/2016 | Stewart |
| 2017/0151446 | A1* | 6/2017 | Redding, Jr. ............ A61N 7/00 |
| 2017/0333109 | A1* | 11/2017 | Gilbert ............... A61B 18/1206 |
| 2018/0256242 | A1* | 9/2018 | Bluvshtein ........ H02M 7/53871 |
| 2020/0155837 | A1 | 5/2020 | Kim |

FOREIGN PATENT DOCUMENTS

| | | |
|---|---|---|
| JP | H10094545 A | 10/1999 |
| JP | 2014507175 A | 3/2014 |
| JP | 2019521746 A | 8/2019 |
| WO | 2019185331 A | 10/2019 |

OTHER PUBLICATIONS

Reddy, MD et al., "Pulsed Field Ablation for Pulmonary Vein Isolation in Atrial Fibrillation," Journal of the American College of Cardiology, 74:3, 2019.

Mujovic et al., "Catheter Ablation of Atrial Fibrillation: An Overview for Clinicians," Adv. Ther. 34: 1897-1917, 2017.

World Health Organization Study: Atrial Fibrillation is a Growing Global Health Concern, Dec. 17, 2013.

Search Report from corresponding Japanese Patent Application No. 2022-533513 dated Aug. 18, 2023.

* cited by examiner

GENERATING IRREVERSIBLE ELECTROPORATION AND RADIOFREQUENCY-ABALTION (IRE/RFA) WAVEFORMS

CROSS-REFERENCE TO RELATED APPLICATION

This application is a continuation application of U.S. application Ser. No. 16/704,421, filed Dec. 5, 2019, which is incorporated herein by reference.

FIELD OF THE INVENTION

The present invention relates generally to methods and systems for combined irreversible electroporation and radiofrequency ablation treatments, and particularly to combined irreversible electroporation and radiofrequency ablation waveform generation.

BACKGROUND OF THE INVENTION

Delivery of radiofrequency (RF) pulses to tissue was previously proposed in the patent literature. For example, U.S. Pat. No. 10,258,406 describes a computer-implemented system for delivering energy to tissue having a necrotic threshold. The system may generally include an electrode array comprising a plurality of electrodes, a central electrode positioned intermediate the plurality of electrodes, and a controller configured to (i) apply a first sequence of electrical pulses to the electrode array to induce thermal heating in the tissue and reduce the necrotic threshold of the tissue, and (ii) apply a second sequence of electrical pulses to the central electrode to induce cell necrosis in the tissue by irreversible electroporation. In an exemplary embodiment, an energy source may be configured to generate electric pulses at frequencies in the range of about 1 Hz to about 10,000 Hz, amplitudes in the range of about +/−100 VDC to about +/−6,000 VDC, and pulse width in the range of about 1 μSec to about 100 mSec. The energy source may be configured to generate the electric pulses suitable to induce thermal heating and pulses suitable to irreversible electroporation in the tissue. The energy source may be operated in biphasic mode and monophasic mode.

As another example, U.S. Pat. No. 10,188,449 describes an electrosurgical generator that includes: a power supply configured to output DC power, an inverter coupled to the power supply, the inverter including a plurality of switching elements, and a controller coupled to the inverter and configured to signal the inverter to simultaneously generate based on the DC power a radio frequency heating waveform and an electroporation waveform. In an exemplary embodiment, a controller coupled to inverter circuitry is configured to signal the inverter circuitry to simultaneously generate, based on the DC power, a radio frequency heating waveform and an electroporation waveform, which is a pulsatile DC waveform configured to generate an electric field and includes a plurality of pulses having an initial pulse with a higher peak voltage and a higher rate of increase of voltage than any subsequent pulse.

U.S. Pat. No. 9,289,606 describes catheter systems that include direction-sensitive, multi-polar tip electrode assemblies for electroporation-mediated therapy, electroporation-induced primary necrosis therapy and electric field-induced apoptosis therapy, including configurations for producing narrow, linear lesions as well as distributed, wide area lesions. For electroporation-induced primary necrosis therapy, a generator may be configured to produce an electric current that is delivered via the electrode assembly as a pulsed electric field in the form of short-duration pulses (e.g., 0.1 to 20 mSec duration) between closely spaced electrodes capable of delivering a relatively low electric field strength (i.e., at the tissue site) of about 0.1 to 1.0 kV/cm. For electric field-induced apoptosis therapy, the generator may be configured to produce an electric current that is delivered as a pulsed electric field in the form of extremely short-duration direct current pulses (e.g., 1 to 300 nSec duration) at a relatively high electric field strength (i.e., at the tissue site) of about 2 to 300 kV/cm. In certain other exemplary embodiments, such as electroporation-mediated ablation therapy, both electroporation specific energy as well as ablation specific energy will be used in the overall process and in such embodiments, the generator may be further configured to deliver ablation energy as well.

SUMMARY OF THE INVENTION

An exemplary embodiment of the present invention provides an irreversible electroporation and radio frequency ablation (IRE/RFA) generator including an IRE pulse generator, harmonic filtration circuitry, and a waveform interleaver. The IRE pulse generator is configured to generate biphasic IRE pulses. The harmonic filtration circuitry is configured to convert the IRE pulses into an RF signal. The waveform interleaver, which is configured to receive the IRE pulses and the RF signal and generate an IRE/RFA output signal by interleaving in alternation one or more of the IRE pulses with one or more periods of the RF signal.

In some exemplary embodiments, the waveform interleaver is configured to receive, from a processor, a setting that specifies an interleaving ratio between the IRE pulses and the periods of the RF signal, and to generate the interleaved IRE/RFA output signal responsively to the setting.

In some exemplary embodiments, the IRE pulse generator is configured to receive, from a processor, a setting that specifies one or more of a shape, an amplitude and a repetition rate of the IRE pulses, and to generate the biphasic IRE pulses responsively to the setting.

In an exemplary embodiment, the harmonic filtration circuitry is configured to receive, from a processor, a setting that specifies one or more of a frequency and amplitude of the RF signal, and to convert the IRE pulses into the RF signal responsively to the setting.

In an exemplary embodiment, the IRE/RFA generator further includes IRE pulse shaping circuitry, configured to apply a prespecified pulse-shape to the IRE pulses.

In some exemplary embodiments, the waveform interleaver is configured to interleave the IRE pulses with the RF signal in accordance with a configurable treatment protocol.

There is additionally provided, in accordance with another exemplary embodiment of the present invention, a method of generation of irreversible electroporation and radio frequency ablation (IRE/RFA) signals, the method including generating biphasic IRE pulses. Using harmonic filtration circuitry, the IRE pulses are converted into an RF signal. an IRE/RFA output signal is generated by interleaving one or more of the IRE pulses with one or more periods of the RF signal.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
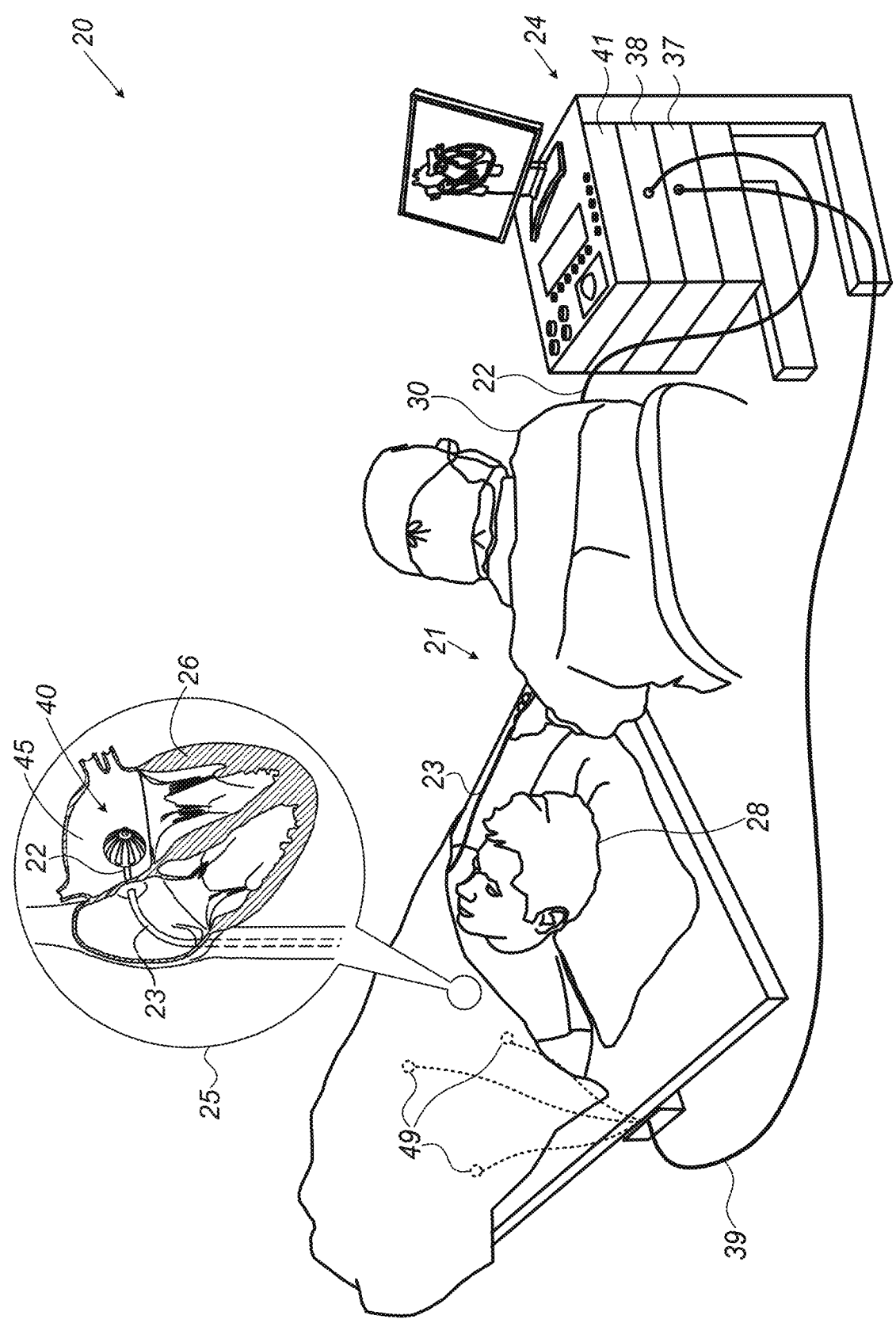
FIG. 1 is a schematic, pictorial illustration of a catheter-based IRE/RFA system, in accordance with an exemplary embodiment of the present invention.

Radiofrequency ablation (RFA) and irreversible electroporation (IRE), which are used as invasive therapeutic modalities, may have complimentary clinical attributes. RFA destroys tissue cells with heat by dissipating electrical energy in tissue, whereas IRE destroys tissue cells by subjecting tissue to strong electric field pulses, with minimal dissipation of electrical energy in tissue.

It is anticipated that, by combining IRE and RFA, a more effective treatment may be achieved. For example, thermally assisted IRE may lead to a more complete ablation, in which tissue insufficiently destroyed by one modality, due to, for example, tissue geometry and/or composition, will be subsequently fully destroyed by the other modality. However, delivering the aforementioned treatments, one after the other, may not be as effective in some applications, such as cardiac treatments, due to, for example, cardiac motion.

Exemplary embodiments of the present invention that are described hereinafter provide systems and methods for joint delivery of IRE and RFA treatments to the same location. In the disclosed technique, also named hereinafter "IRE/RFA," sequences of IRE and RFA waveforms that are intertwined, interweaved and/or interleaved on a sub-second scale are generated and delivered. In an exemplary embodiment, IRE pulses and RFA cycles are applied to the same tissue location at the same time by interleaving one or more IRE pulses with one or more RFA cycles on the same ablation electrode, according to a preset interleaving ratio.

In some exemplary embodiments, a generator is provided that can vary its output sequence of waveforms to apply only IRE pulses, only RF cycles, or sequences of M IRE pulses and N RFA cycles in alternation, with M≥1, N≥1.

Other properties of the sequence may be configured through a processor that controls the generator, for example, IRE pulse shape and amplitude, and pulse repetition rate, as well RFA parameters, such as RF frequency. Typically, for IRE, the generator is able to generate biphasic pulses with peak to peak voltages of up to 4 kV, and at typical pulse widths of μSec. For RFA, the generator is able to generate sinusoidal cycles with peak to peak voltages of up to 100V with mSec periodicity.

In some exemplary embodiments, an operator of the disclosed generator, e.g., using a user interface in a processor, may select, for example, an energy scale, such as 100 percent IRE (represented by N=0), 100 percent RFA (represented by M=0), or any ratio in between. The generator is programmed to provide, for example using a configurable protocol, the correct sequence of {M, N} interleaved waveforms according to the operator selection. Such a configurable protocol may further include, for example, pulse width and pulse amplitude that yield the required selection.

In some exemplary embodiments, the disclosed generator produces an RF signal (e.g., cycles) from IRE pulses using (a) harmonic filtration circuitry, and (b) IRE/RFA switching circuitry, both included in the disclosed generator. To generate waveforms for RFA, the disclosed harmonic filtration may apply, to an IRE waveform, one or more of the following according to a given embodiment: low-pass filtration, band-pass filtration, or band-stop filtration.

The disclosed IRE/RPA generator enables the application of IRE and RFA treatments to the same location at the same time, and thus may improve the clinical outcome of invasive treatments of cardiac arrhythmia.

System Description

FIG. 1 is a schematic, pictorial illustration of a catheter-based IRE/RFA system 20, in accordance with an exemplary embodiment of the present invention. System 20 comprises a catheter 21, wherein a shaft 22 of the catheter is inserted into a heart 26 of a patient 28 through a sheath 23. The proximal end of catheter 21 is connected to a console 24.

Console 24 comprises an IRE/RFA generator 38 for applying intertwined IRE/RFA waveforms via catheter 21 to ablate tissue in a left atrium 45 of heart 26. In the exemplary embodiment described herein, catheter 21 may be used for any suitable therapeutic and/or diagnostic purpose, such as electrical sensing and/or isolation of ostium tissue of a pulmonary vein in left atrium 45 of heart 26.

A physician 30 inserts shaft 22 through the vascular system of patient 28. As seen in inset 25, an inflatable balloon 40 is fitted at the distal end of shaft 22. During the insertion of shaft 22, balloon 40 is maintained in a collapsed configuration inside sheath 23. By containing balloon 40 in a collapsed configuration, sheath 23 also serves to minimize vascular trauma along the way to the target location. Physician 30 navigates the distal end of shaft 22 to a target location in heart 26.

Once the distal end of shaft 22 has reached the target location, physician 30 retracts sheath 23 to expand balloon 40. Physician 30 then manipulates shaft 22 such that electrodes disposed on balloon 40 engage an interior wall of the ostium.

Console 24 comprises a processor 41, typically a general-purpose computer, with suitable front end and interface circuits 37 for receiving signals from catheter 21 and from external-electrodes 49, which are typically placed around the chest of patient 26. For this purpose, processor 41 is connected to external electrodes 49 by wires running through a cable 39. In an exemplary embodiment, physician 30 diagnoses an arrhythmogenic tissue location, using, for example, electrophysiological signals acquired by catheter 21. Subsequently, physician 30 applies, via the electrodes disposed on balloon 40, an intertwined IRE/RFA waveform to ablate tissue.

Processor 41 is typically programmed (software) to carry out the functions described herein. The software may be downloaded to the computer in electronic form, over a network, for example, or it may, alternatively or additionally, be provided and/or stored on non-transitory tangible media, such as magnetic, optical, or electronic memory.

Although the illustrated exemplary embodiment relates specifically to the use of a balloon for ablation of heart tissue, the elements of system 20 and the methods described herein may alternatively be applied in controlling ablation using other sorts of multi-electrode ablation devices, such as multi-arm ablation catheters. In other words, any suitable device may be utilized in accordance with the present invention.

Generation of Sequence of Interleaved IRE/RFA Waveforms

Figure 2:
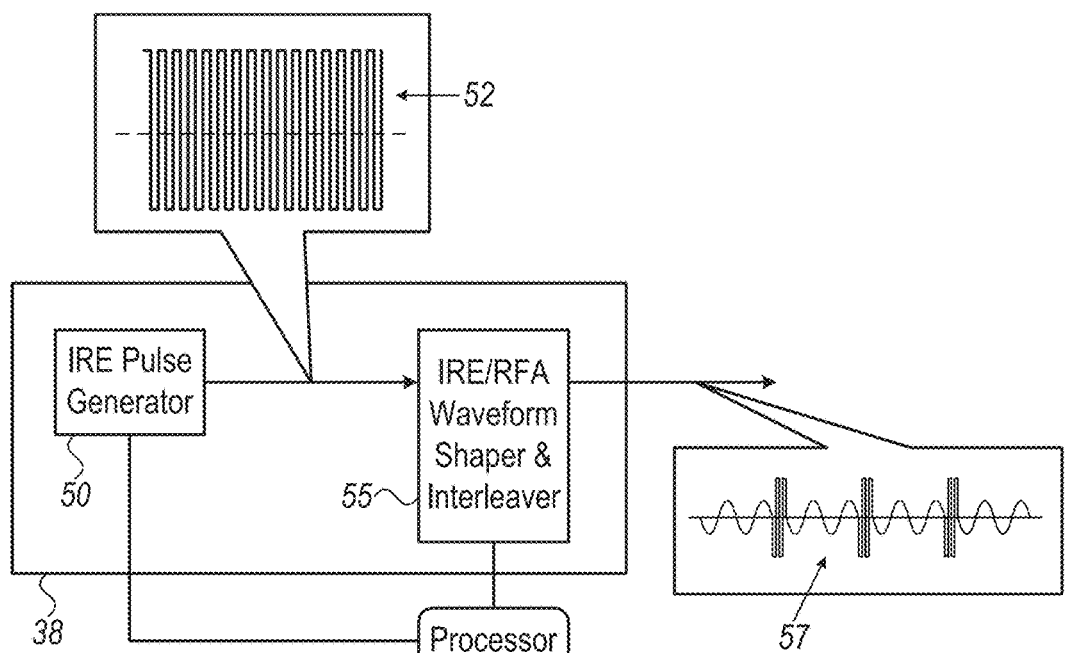
FIG. 2 is a schematic block diagram of the IRE/RFA generator of the system of FIG. 1, in accordance with an exemplary embodiment of the present invention.

FIG. 2 is a schematic block diagram of IRE/RFA generator 38 of the system 20 illustrated in FIG. 1, in accordance with an exemplary embodiment of the present invention. In the illustrated exemplary embodiment, generator 38 comprises an IRE pulse generator 50 and an IRE/RFA waveform shaper and interleaver 55, which are both configurable and controlled by processor 41.

As illustrated, IRE pulse generator 50 generates a sequence 52 of high-voltage IRE biphasic pulses of a predefined waveform. In the present context, the term "biphasic pulse" refers to a pulse having a positive-voltage phase and a negative-voltage phase, such that the average voltage of the pulse is zero volts. In an exemplary embodiment, but not necessarily, the biphasic pulses have a square-wave pulse-shape. In some exemplary embodiments, the peak-to-peak voltage of the biphasic pulse is on the order of up to 4 KV, i.e., ±2 KV. The pulse width of each biphasic pulse is typically on the order of several microseconds. Alternatively, any other suitable pulse parameters may be used.

Figure 3:
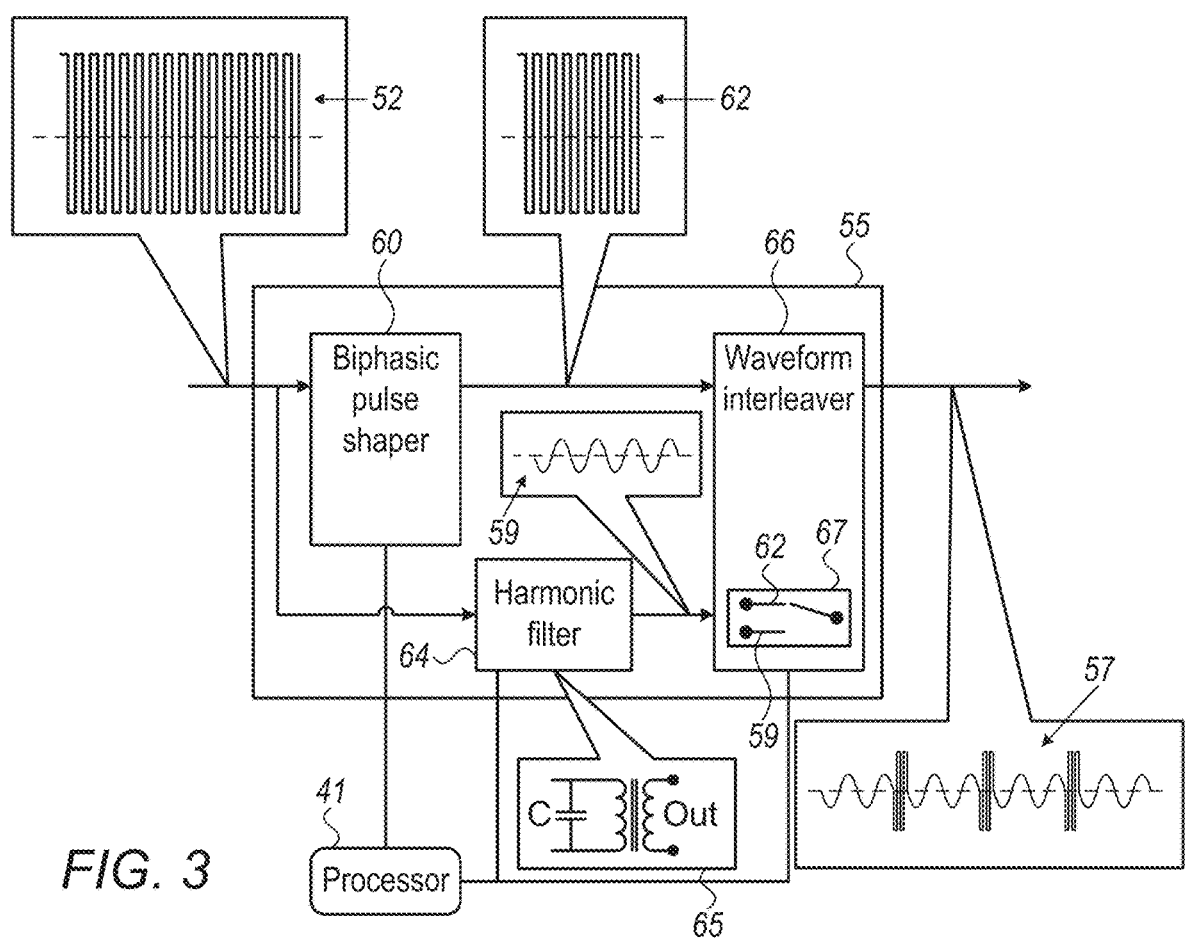
FIG. 3 is a schematic block diagram showing certain details of the IRE/RFA generator of FIG. 2, in accordance with an exemplary embodiment of the present invention.

IRE/RFA waveform shaper and interleaver 55, further described in FIG. 3, converts input sequence 52 into an interleaved IRE/RFA sequence 57 of output waveforms comprising, by way of example, M=2 IRE shape pulses interleaved with N=2 sinusoidal periods (e.g., two sinus shaped pulses) of RF energy. IRE/RFA sequence 57 is typically delivered to catheter 22, for application to a selected tissue location via an ablation electrode as described above with reference to FIG. 1.

FIG. 3 is a schematic block diagram showing certain details of IRE/RFA generator 38 of FIG. 2, in accordance with an exemplary embodiment of the present invention. In the present example, IRE/RFA waveform shaper and pulse interleaver 55 comprises biphasic pulse shaper circuitry 60, harmonic filter circuitry 64, and waveform interleaver circuitry 66.

Biphasic pulse shaper circuitry 60 is configured to adapt IRE pulses of sequence 52, if required, to IRE pulses 62 having a final shape and repetition rate. For example, pulse shaper 60 may comprise an array of capacitors for producing different rise times and/or fall times of the biphasic pulses.

Harmonic filter circuitry 64 may comprise a set of harmonic filters of some of the types described above, and may be configured, based on settings provided by processor 41, to convert the input IRE pulses of sequence 52 into an RF signal 59, typically a sinusoidal signal. RF signal 59 typically has a frequency on the order of 450 kHz-500 kHz and peak-to-peak voltage on the order of up to 100V (i.e., ±50V). Alternatively, however, any other suitable signal parameters may be used.

As seen in an inset 65, harmonic filtration may be performed by a low pass filter (represented by a capacitor), while output voltage is determined using one or more transformers. Finally, waveform interleaver 66 interleaves one or more IRE pulses 62 with one or more periods of RF signal 59 and outputs the interleaved sequence 57 to catheter 21. As seen, waveform interleaver 66 comprises a switching circuitry 67 to switch between input waveforms 59 and 62.

Harmonic filtration is one of the simplest ways in which to convert a square wave into a sine wave. A square wave consists of a fundamental frequency and higher order harmonics. The harmonic filtration serves to remove the higher order harmonics thereby leaving the sinusoidal fundamental frequency signal.

The exemplary configurations shown in FIGS. 2 and 3 are chosen purely for the sake of conceptual clarity. In alternative exemplary embodiments, the disclosed techniques may use any other suitable pulse generation and shaping schemes.

Figure 4:
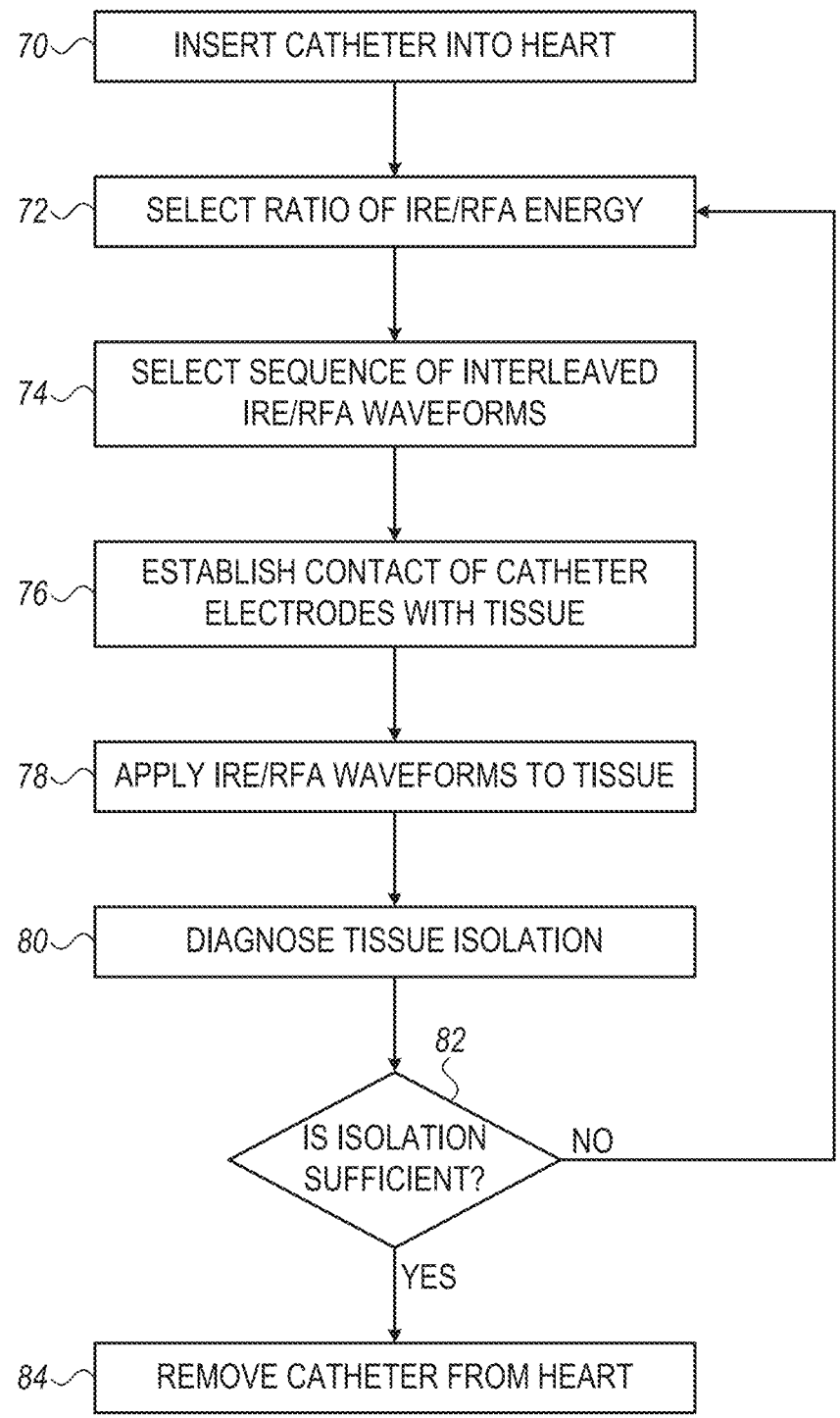
FIG. 4 is a flow chart that schematically illustrates a method for IRE/RFA treatment using the IRE/RFA system of FIG. 1, in accordance with an exemplary embodiment of the present invention.

FIG. 4 is a flow chart that schematically illustrates a method for IRE/RFA treatment using IRE/RFA system 20 of FIG. 1, in accordance with an exemplary embodiment of the present invention. The process begins with physician 30 inserting catheter 20 into heart 26, at a catheter insertion step 70. Next, physician 30 selects a ratio of IRE/RFA energy to be delivered to the target tissue, for example, by selecting a predefined protocol, at a therapeutic energy selection step, 72. As noted above, physician 30 may select any ratio between 100 percent IRE energy to 100 percent RFA energy, depending on the clinical target.

Assuming physician 30 chooses to apply a mixture of IRE and RFA energy, physician 30 specifies an interleaved sequence of IRE/RFA waveforms, for example, as specified by the selected protocol, at an interleaved sequence selection step, 74. For example, physician 30 may select an {M=1, N=1} sequence, as defined above, which has a maximal degree of interleaving.

Next, at catheter positioning step 76, physician 30 manipulates catheter 21 to establish contact between electrodes disposed on balloon 40 and tissue, such as of an ostium of a pulmonary vein. Next, physician 30 applies the selected interleaved sequence of IRE/RFA waveforms to tissue, at an IRE/RFA treatment step 78.

Immediately after treatment, at a post IRE/RFA treatment diagnostic step 80, physician 30 uses balloon 40 as a diagnostic catheter to acquire electrograms to check to what extent treatment step 78 achieved isolation. If, at a checking step 82, the physician finds that sufficient isolation was achieved, physician 30 then removes the catheter from the patient body, at a catheter retraction step 84. Otherwise, physician 30 may reposition the balloon for additional treatment by looping back to step 72 to select parameters of the additional treatment step.

Although the embodiments described herein mainly address cardiac applications, the methods and systems described herein can also be used in other medical applications, such as in treatment of solid tumors, such as in lungs or liver.

It will thus be appreciated that the exemplary embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for combining irreversible electroporation and radio frequency ablation (IRE/RFA), comprising:
   an IRE pulse generator configured to generate biphasic IRE square pulses;
   a biphasic pulse shaper, configured and controlled by a processor, to adapt the biphasic IRE square pulses to IRE pulses having a final shape and repetition rate;

one or more harmonic filters, configured and controlled by the processor, to convert the biphasic IRE square pulses into an RF sinusoidal signal; and a waveform interleaver comprising switching circuitry, which is configured and controlled by the processor, to receive the IRE square pulses and the converted RF sinusoidal signal and generate an output signal having a composition comprising one of: i) the adapted IRE pulses having a final shape and repetition rate, ii) the converted RF sinusoidal signal, or iii) a combined IRE/RFA output signal that switches between the adapted IRE square pulses and the converted RF sinusoidal signal.

2. The system of claim 1, wherein the combined IRE/RFA output signal comprises one or more of the IRE square pulses with one or more periods of the converted RF sinusoidal signal interleaved in alternation into a single waveform.

3. The system of claim 1, wherein the composition of the generated output signal is one-hundred percent (100%) IRE square pulses.

4. The system of claim 1, wherein the composition of the generated output signal is one-hundred percent (100%) converted RF sinusoidal signal.

5. The system of claim 1, wherein the composition of the generated output signal is a ratio between one-hundred percent (100%) IRE square pulses and one-hundred percent (100%) converted RF sinusoidal signal.

6. A method for combining irreversible electroporation and radio frequency ablation (IRE/RFA), comprising:
generating biphasic IRE square pulses;
adapting the biphasic IRE square pulses to IRE pulses having a final shape and repetition rate;
using one or more harmonic filters, configured by a processor, converting the IRE square pulses into an RF sinusoidal signal; and
receiving the IRE square pulses and the converted RF sinusoidal signal and generating, by a waveform interleaver comprising switching circuitry controlled by the processor, in response to receiving an input via a user interface, an output signal having a composition comprising one of: i) the adapted IRE pulses having a final shape and repetition rate, ii) the converted RF sinusoidal signal, or iii) a combined IRE/RFA output signal that switches between the adapted IRE square pulses and the converted RF sinusoidal signal.

7. The method of claim 6, wherein the combined IRE/RFA output signal comprises one or more of the IRE square pulses with one or more periods of the converted RF sinusoidal signal interleaved in alternation into a single waveform.

8. The method of claim 6, wherein the composition of the generated output signal is one-hundred percent (100%) IRE square pulses.

9. The method of claim 6, wherein the composition of the generated output signal is one-hundred percent (100%) converted RF sinusoidal signal.

10. The method of claim 6, wherein the composition of the generated output signal is a ratio between one-hundred percent (100%) IRE square pulses and one-hundred percent (100%) converted RF sinusoidal signal.

11. A computer program product, comprising a non-transitory computer-readable medium having computer-readable program code embodied therein to be executed by one or more processors, the program code including instructions to:
cause biphasic IRE square pulses to be generated;
cause the biphasic IRE square pulses to be adapted to IRE pulses having a final shape and repetition rate;
cause, using one or more harmonic filters, the IRE square pulses to be converted into an RF sinusoidal signal; and
receive the IRE square pulses and the converted RF sinusoidal signal and generate, by a waveform interleaver comprising switching circuitry controlled by the processor, in response to receiving an input via a user interface, an output signal having a composition comprising one of: i) the adapted IRE pulses having a final shape and repetition rate, ii) the converted RF sinusoidal signal, or iii) a combined IRE/RFA output signal that switches between the adapted IRE square pulses and the converted RF sinusoidal signal.

12. The computer program product of claim 11, wherein the combined IRE/RFA output signal comprises one or more of the IRE square pulses with one or more periods of the converted RF sinusoidal signal interleaved in alternation into a single waveform.

13. The computer program product of claim 11, wherein the composition of the generated output signal is one-hundred percent (100%) IRE square pulses.

14. The computer program product of claim 11, wherein the composition of the generated output signal is one-hundred percent (100%) converted RF sinusoidal signal.

15. The computer program product of claim 11, wherein the composition of the generated output signal is a ratio between one-hundred percent (100%) IRE square pulses and one-hundred percent (100%) converted RF sinusoidal signal.

* * * * *